(12) United States Patent
Piantoni et al.

(10) Patent No.: US 10,470,941 B2
(45) Date of Patent: Nov. 12, 2019

(54) METHOD FOR MAKING ABSORBENT SANITARY ARTICLES

(71) Applicant: GDM S.p.A., Bologna (IT)

(72) Inventors: Matteo Piantoni, Albino (IT); Valerio Soli, Bologna (IT)

(73) Assignee: GDM S.p.A., Bologna (IT)

( * ) Notice: Subject to any disclaimer, the term of this patent is extended or adjusted under 35 U.S.C. 154(b) by 114 days.

(21) Appl. No.: 15/518,153

(22) PCT Filed: Oct. 22, 2015

(86) PCT No.: PCT/IB2015/058161
§ 371 (c)(1),
(2) Date: Apr. 10, 2017

(87) PCT Pub. No.: WO2016/067169
PCT Pub. Date: May 6, 2016

(65) Prior Publication Data
US 2017/0304125 A1    Oct. 26, 2017

(30) Foreign Application Priority Data

Oct. 27, 2014 (IT) .............................. B02014A0597

(51) Int. Cl.
A61F 13/15        (2006.01)
A61F 13/49        (2006.01)
A61F 13/56        (2006.01)

(52) U.S. Cl.
CPC .. *A61F 13/15756* (2013.01); *A61F 13/15577* (2013.01); *A61F 13/15699* (2013.01); *A61F 13/49009* (2013.01); *A61F 13/56* (2013.01)

(58) Field of Classification Search
CPC .......... A61F 13/15723; A61F 13/15577; A61F 13/15756; A61F 13/56; A61F 13/49009; A61F 2013/15821
See application file for complete search history.

(56) References Cited

U.S. PATENT DOCUMENTS 9,433,538 B2 * 9/2016 Pagel ................ A61F 13/15723

FOREIGN PATENT DOCUMENTS

| EP | 1941853 A1 | 7/2008 |
| EP | 1994919 A1 | 11/2008 |
| EP | 2238955 A1 | 10/2010 |

OTHER PUBLICATIONS

International Search Report dated Jan. 21, 2016 for counterpart PCT Application No. PCT/IB2015/058161.

* cited by examiner

*Primary Examiner* — Mark A Osele
*Assistant Examiner* — Christopher C Caillouet
(74) *Attorney, Agent, or Firm* — Shuttleworth & Ingersoll, PLC; Timothy J. Klima

(57) ABSTRACT

A method for making sanitary articles, includes: feeding along a longitudinal direction of movement a first web of material defining a main body of the article; feeding a pair of longitudinal strips; dividing each strip into a succession of trapezoidal pieces adjacent each other and each having a long base and a short base so the pieces of each strip can be divided alternately into first pieces having a first orientation and second pieces having a second orientation opposite to the first orientation; spacing the pieces of each strip from each other; rotating the first or second pieces of each strip by 180° in plane to give the pieces of the first strip the first orientation and the pieces of the second strip the second orientation; applying each piece on a first face so the long base protrudes laterally from the edge of the first web.

16 Claims, 10 Drawing Sheets

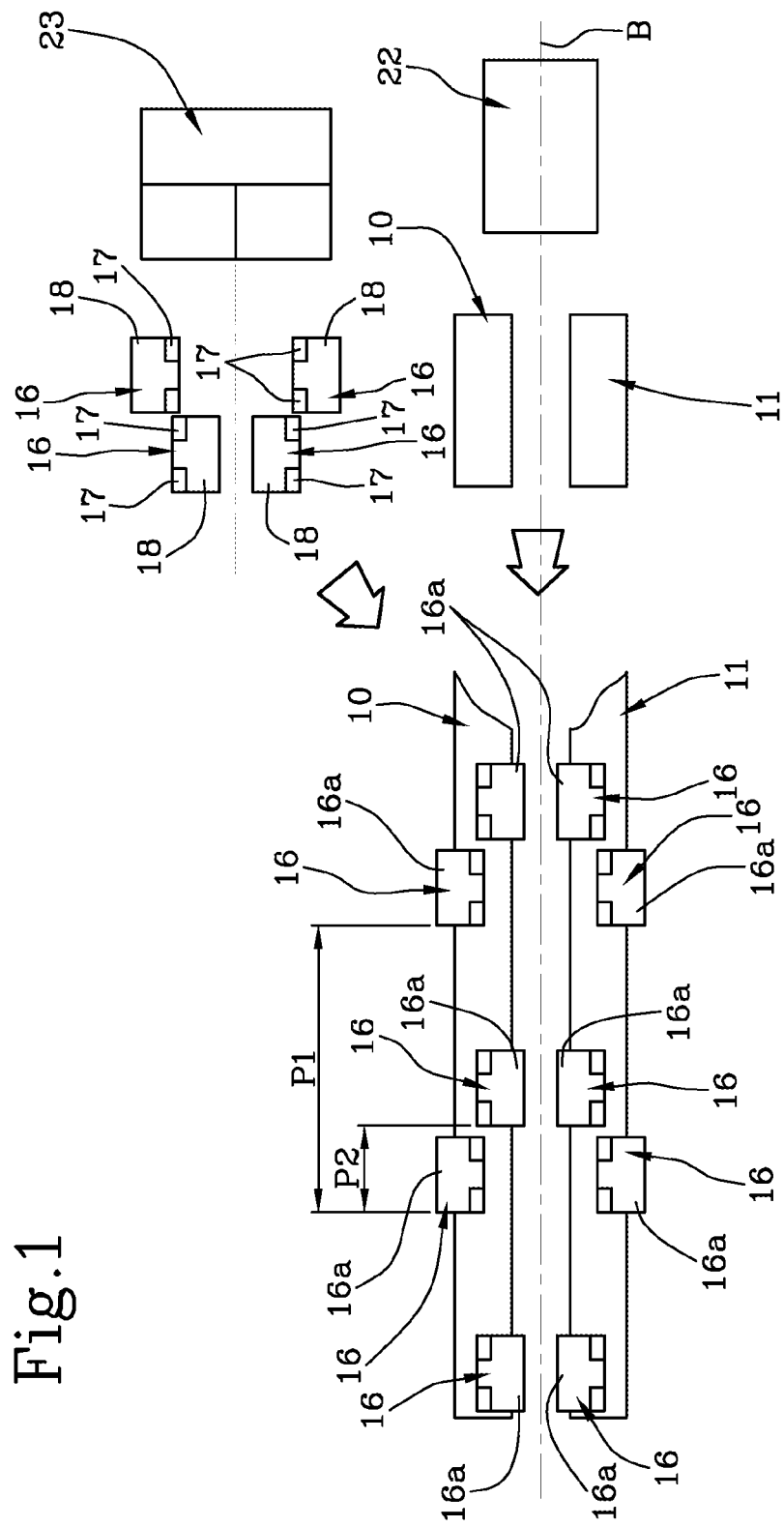

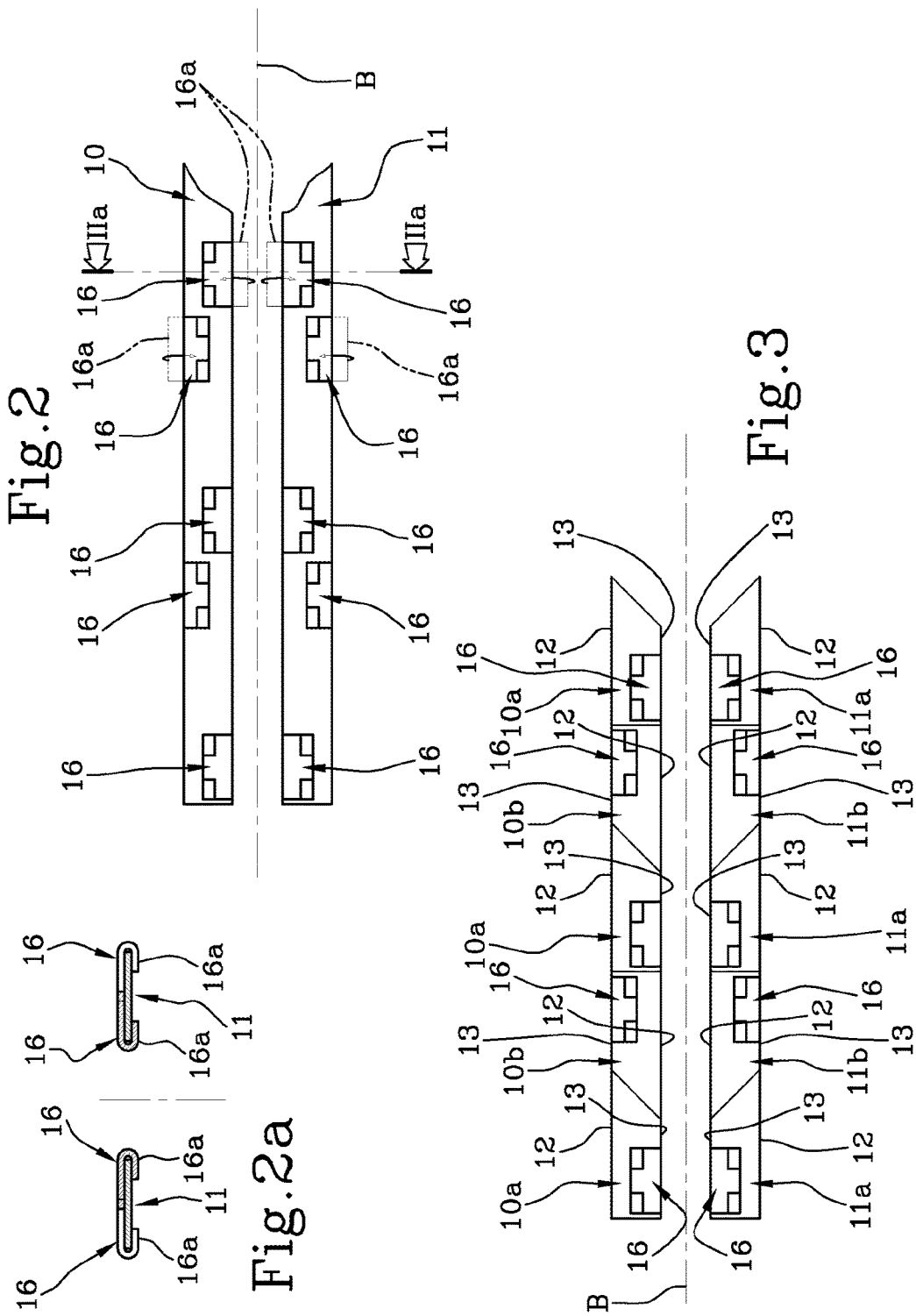

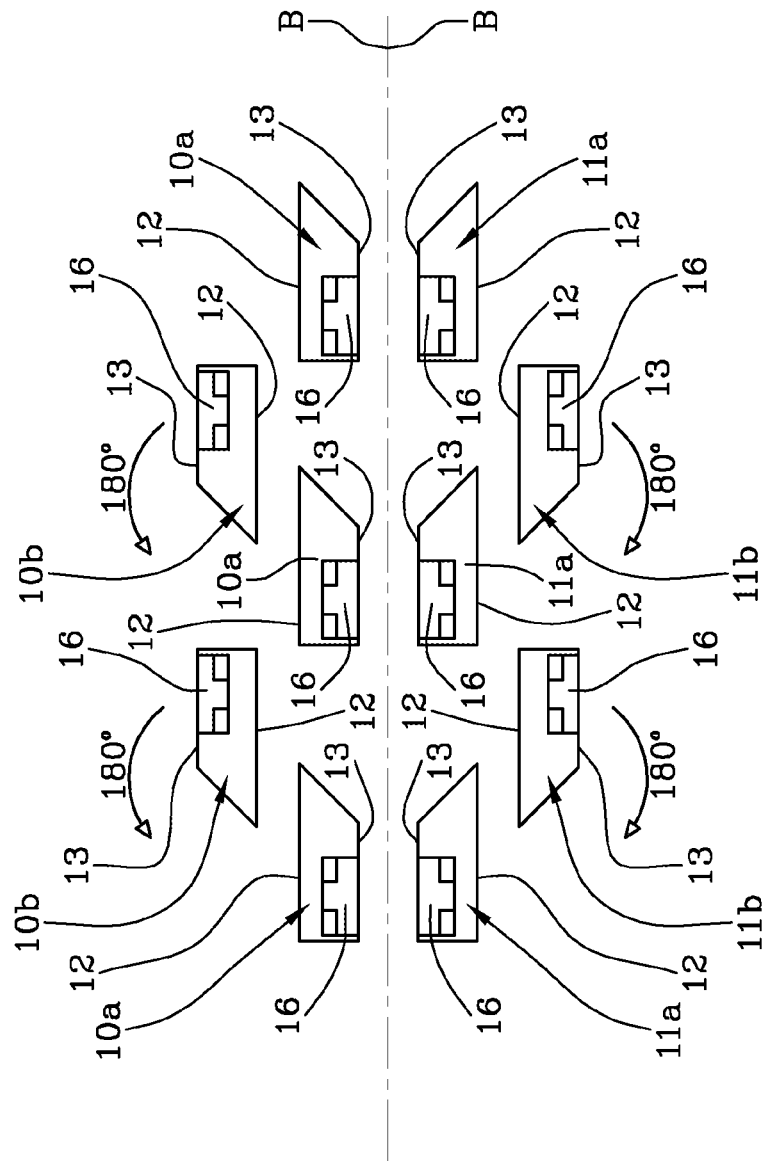

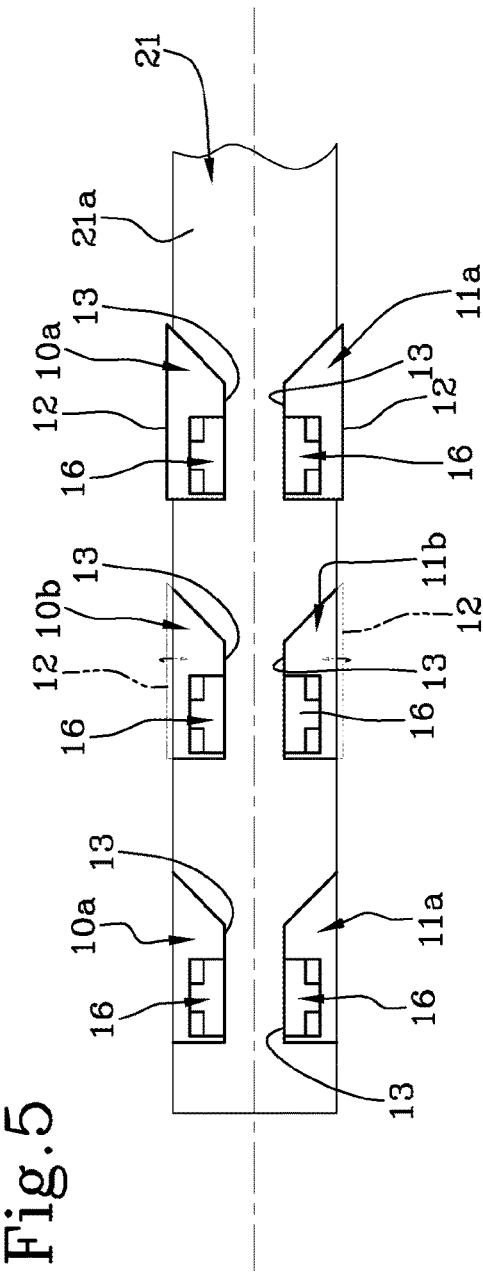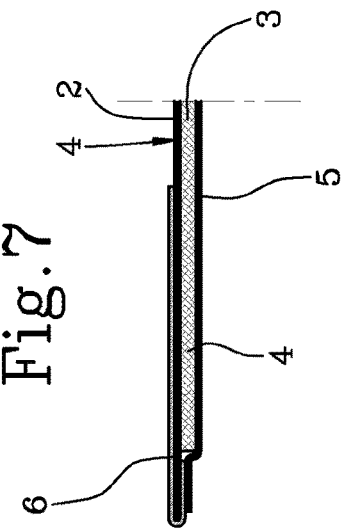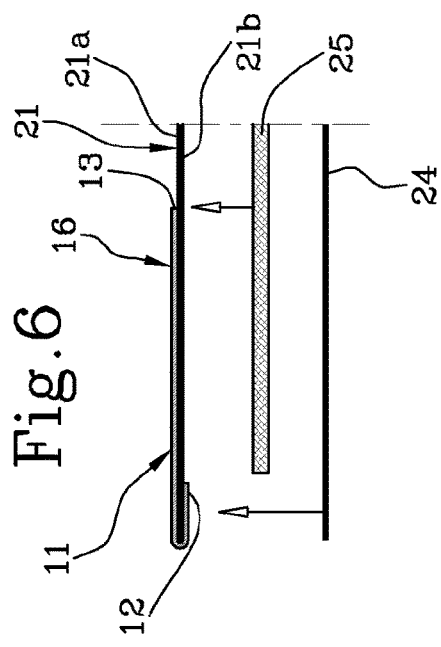

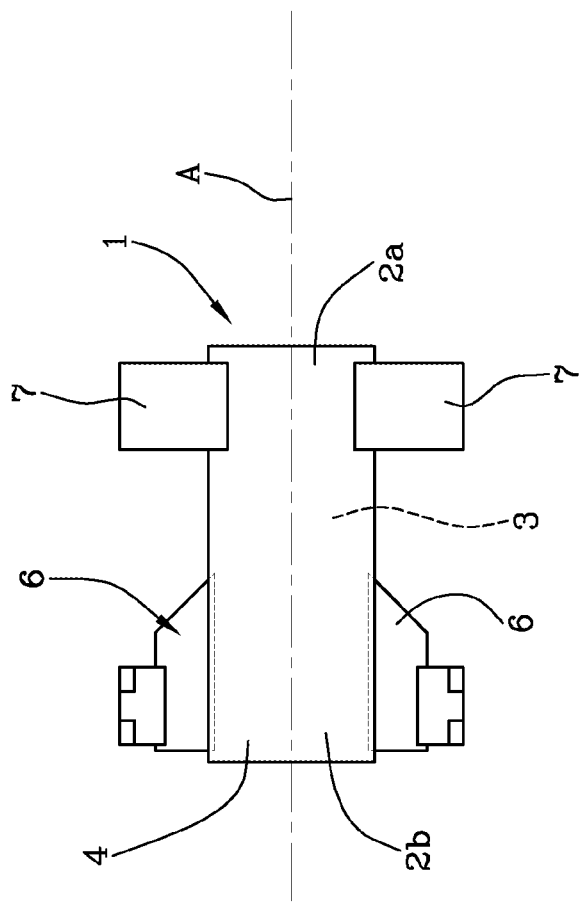

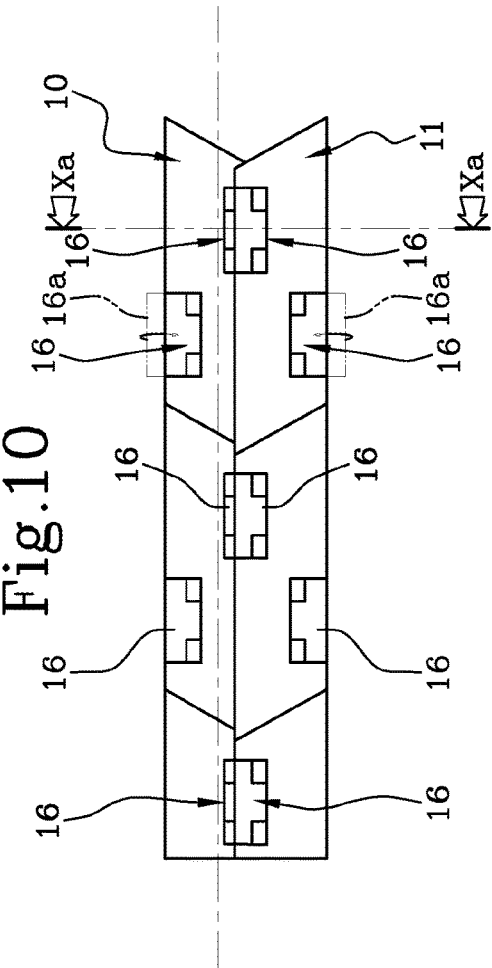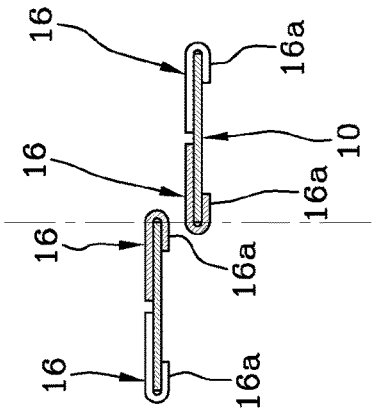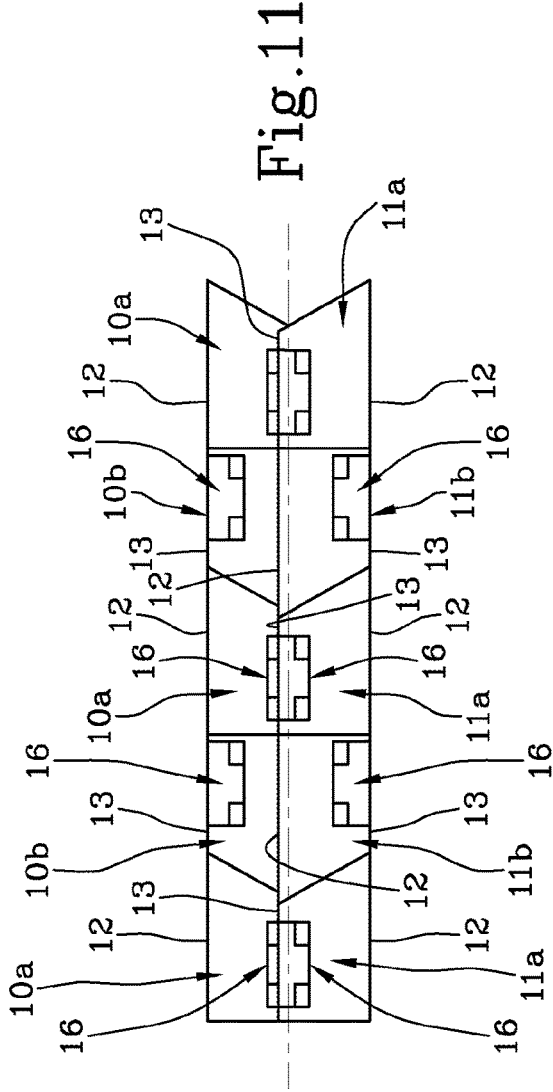

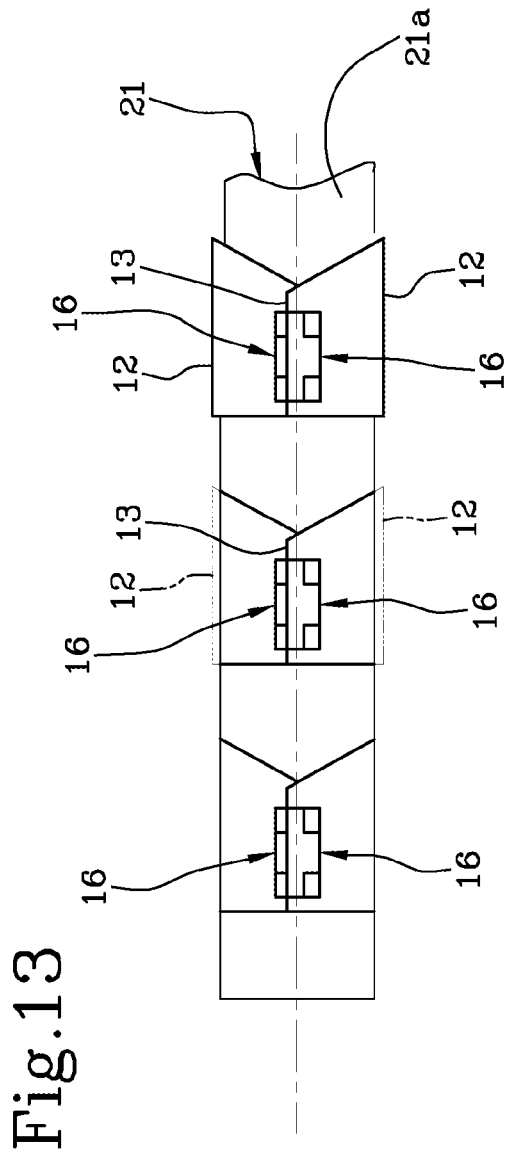
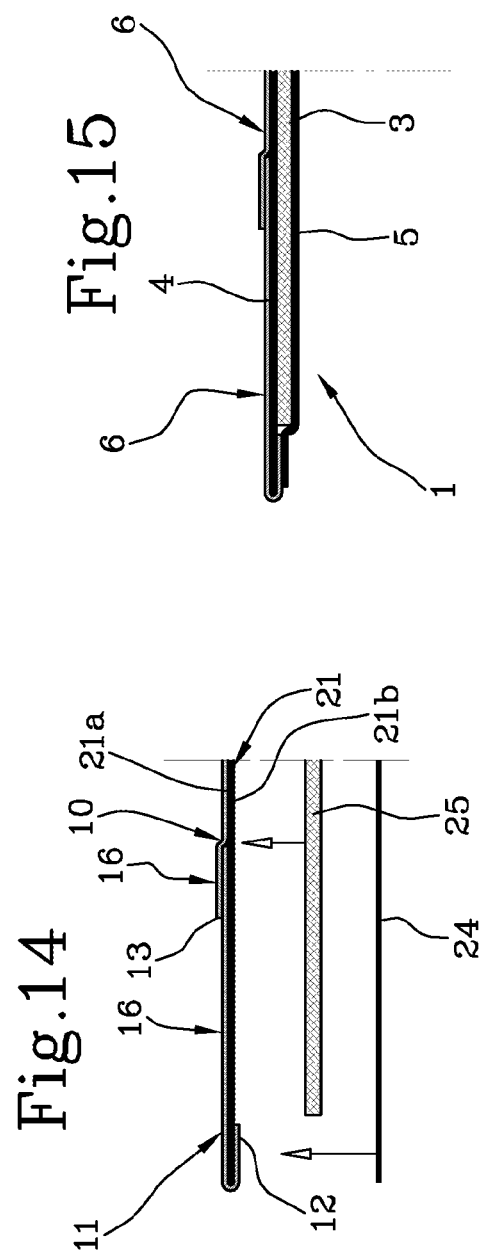

METHOD FOR MAKING ABSORBENT SANITARY ARTICLES

This application is the National Phase of International Application PCT/IB2015/058161 filed Oct. 22, 2015 which designated the U.S.

This application claims priority to Italian Patent Application No. BO2014A000597 filed Oct. 27, 2014, which application is incorporated by reference herein.

TECHNICAL FIELD

This invention relates to a method for making absorbent sanitary articles. The invention is therefore applicable in particular to the sector of automatic machines, and in particular for the production of absorbent sanitary articles such as disposable nappies for children or adults.

BACKGROUND ART

Various methods are known in the prior art for making absorbent sanitary articles, and in particular for joining separate accessory elements, such as, for example, closing flaps, to the main portion, that is, the absorbent portion (or core) of the article.

It should be noted that, in recent years, the development of the technology has increasingly led to the design of production lines which are able to minimize the waste material which is obtained as a result of the numerous cutting operations performed during processing.

In this regard, numerous patent publications describe processes which, starting from two or more webs of elastic material, make cuts such as to define pieces of web having geometrical shapes which are interpenetrating with alternating orientations.

The pieces can therefore be applied directly to the supporting web (chassis) following suitable rotations or translations, avoiding the production of waste and also allowing the "leg opening" of the absorbent article to be obtained.

For example, patent document EP1941853 describes a method for making absorbent sanitary articles where the flaps are made from a pair of parallel webs of elastic material, which are cut in such a way that each of them is divided into an alternating succession of first and second pieces which are trapezoidal in shape.

More specifically, the pieces of the first web are mirror-symmetrical to the pieces of the second web.

In the first pieces of both the webs, the long bases face each other, whilst in the second pieces, the short bases are facing each other.

In order to apply the flaps in the correct direction (that is, with the long bases facing each other), the method comprises rotating each of the second pieces of both of the webs by 180° so as to obtain an ordered succession of pairs of pieces having the same orientation, such as to allow a direct application of the pieces, that is to say, the flaps, to the continuous supporting web.

Another solution is known from patent document EP1994919, where the two webs are cut in an equivalent fashion, not mirror-symmetrical, that is to say, in such a way that each short base of a piece of the first web faces the long base of a corresponding piece of the second web.

In other words, each web has a plurality of first pieces, whose long base is oriented towards the other web, and a plurality of second pieces, whose short base is oriented towards the other web.

In order to obtain a correct orientation of the flaps, the method comprises a step of rotating all the second pieces of both webs, which unlike the method described above are alternating, but which, once rotated, similarly define an ordered succession of pairs of pieces having the same orientation.

Disadvantageously, these methods are difficult to implement in the production of nappies for adults, in which the size of the flaps (or pieces) prevents handling and positioning in the "traditional" manner.

Moreover, it should be noted that the methods in question require the flaps to be positioned and fixed directly on the outside face of the chassis, by gluing or other similar processes, in order to guarantee that the flaps maintain their position even after a pulling action (that is, in use).

DISCLOSURE OF THE INVENTION

For this reason, the aim of this invention is to provide a method for making absorbent sanitary articles which can overcome the above-mentioned drawbacks of the prior art.

More specifically, the aim of this invention is to provide a method for making absorbent sanitary articles which can be used for the production of nappies both for children and for adults.

Moreover, the aim of this invention is to provide a method for making absorbent sanitary articles which is able to limit the footprint of the production line which implements the method.

The aim of this invention is also to provide a method which is able to make an absorbent article where the flaps are firmly secured to the chassis.

These aims are achieved by a method for making absorbent sanitary articles comprising the steps described in one or more of the appended claims, and in particular:

feeding along a longitudinal direction of movement at least a first continuous web of material suitable for defining at least part of the main body of an absorbent sanitary article;

feeding a pair of longitudinal strips;

dividing each strip into a succession of trapezoidal pieces adjacent to each other and each having a long base and a short base, in such a way that the pieces of each strip can be divided alternately into first pieces having a first orientation and second pieces having a second orientation opposite to the first orientation;

spacing the pieces of each strip from each other;

rotating the first or second pieces of each strip by 180° in plane in such a way as to give the pieces of the first strip the first orientation and the pieces of the second strip the second orientation.

According to the invention, the method also comprises the steps of:

applying each piece on a first face, in use, outer face, of the first web, in such a way that the long base of the piece protrudes from the side of the first web;

folding the long base of each piece towards a second face, in use, inner face, of the first web and fixing it to the second face.

Advantageously, the method according to this invention allows making an absorbent article in the minimum of space, so that nappies both for children and for adults can be made in the same way.

Preferably, moreover, the first web is defined by the upper layer of the chassis of the absorbent article, that is, by the top sheet, on which the pieces having a first orientation are placed.

It should be noted that the step of folding the long base beneath the top sheet guarantees that it is, on the finished product, interposed between the top sheet and the back sheet, that is, securely fixed to the chassis without the risk of detachment.

BRIEF DESCRIPTION OF THE DRAWINGS

Further features and advantages of this invention will become more apparent from the following description of a preferred, non limiting example embodiment of a method for making absorbent sanitary articles as illustrated in the accompanying drawings, in which:

FIG. 1 shows a schematic view of a first step of a first embodiment of the method according to this invention;

FIGS. 2 and 2a schematically show a plan view and a cross section of a second step of a first embodiment of the method according to this invention;

FIG. 3 shows a schematic view of a third step of a first embodiment of the method according to this invention;

FIG. 4 shows a schematic view of a fourth step of a first embodiment of the method according to this invention;

FIG. 5 shows a schematic view of a fifth step of a first embodiment of the method according to this invention;

FIG. 6 shows a schematic cross section view of a sixth step of a first embodiment of the method according to this invention;

FIG. 7 shows a schematic cross section view of the result of the step of FIG. 6;

FIG. 8 shows a schematic plan view of an absorbent sanitary article made using the method of FIGS. 1 to 7;

FIGS. 10 and 10a schematically show a plan view and a cross section of a second step of a second embodiment of the method according to this invention;

FIG. 11 shows a schematic view of a third step of a second embodiment of the method according to this invention;

FIG. 13 shows a schematic view of a fifth step of a second embodiment of the method according to this invention;

FIG. 14 shows a schematic cross section view of a sixth step of a second embodiment of the method according to this invention;

FIG. 15 shows a schematic cross section view of the result of the step of FIG. 14;

DETAILED DESCRIPTION OF PREFERRED EMBODIMENTS OF THE INVENTION

Figure 9:
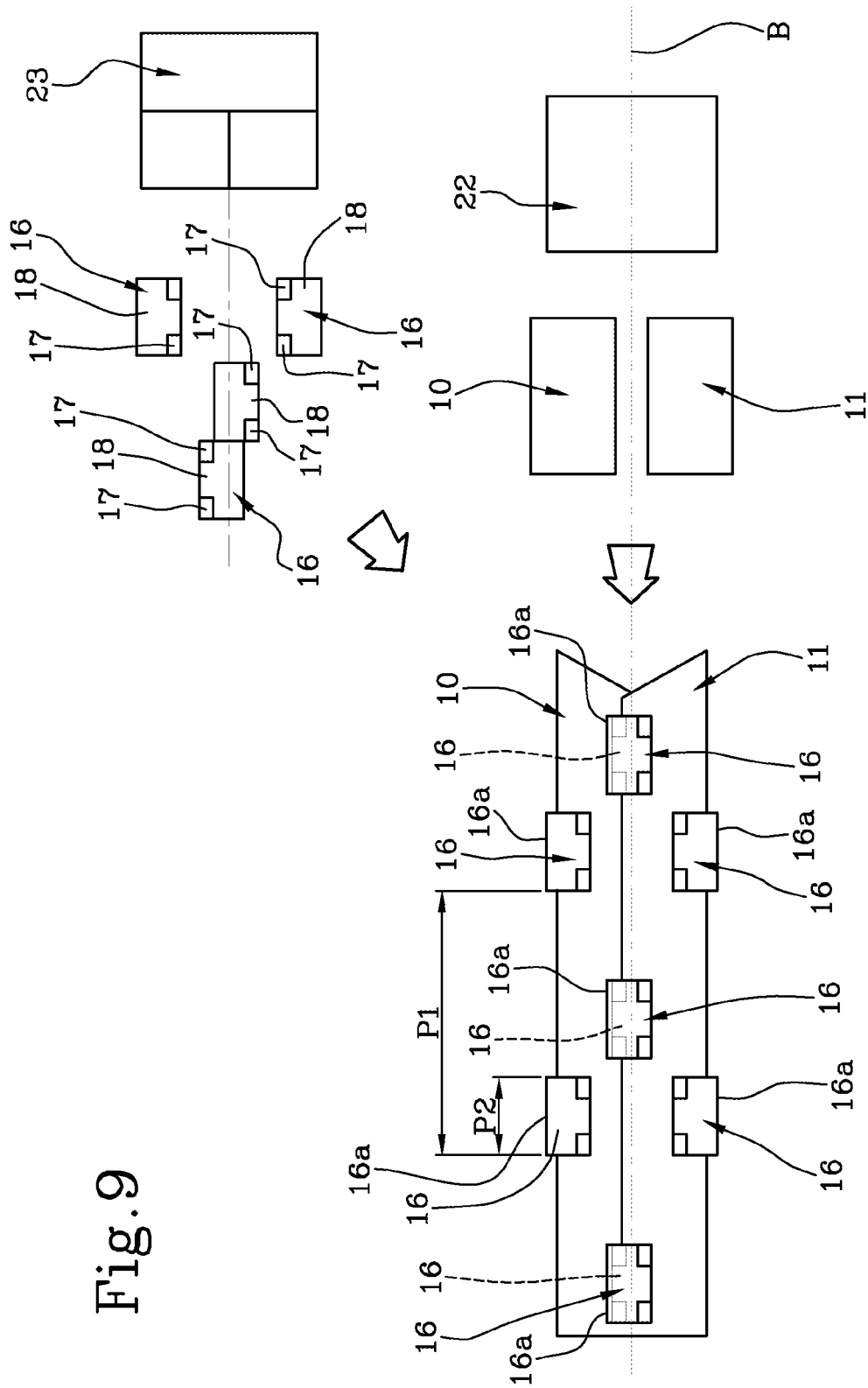
FIG. 9 shows a schematic view of a first step of a second embodiment of the method according to this invention.
Figure 12:
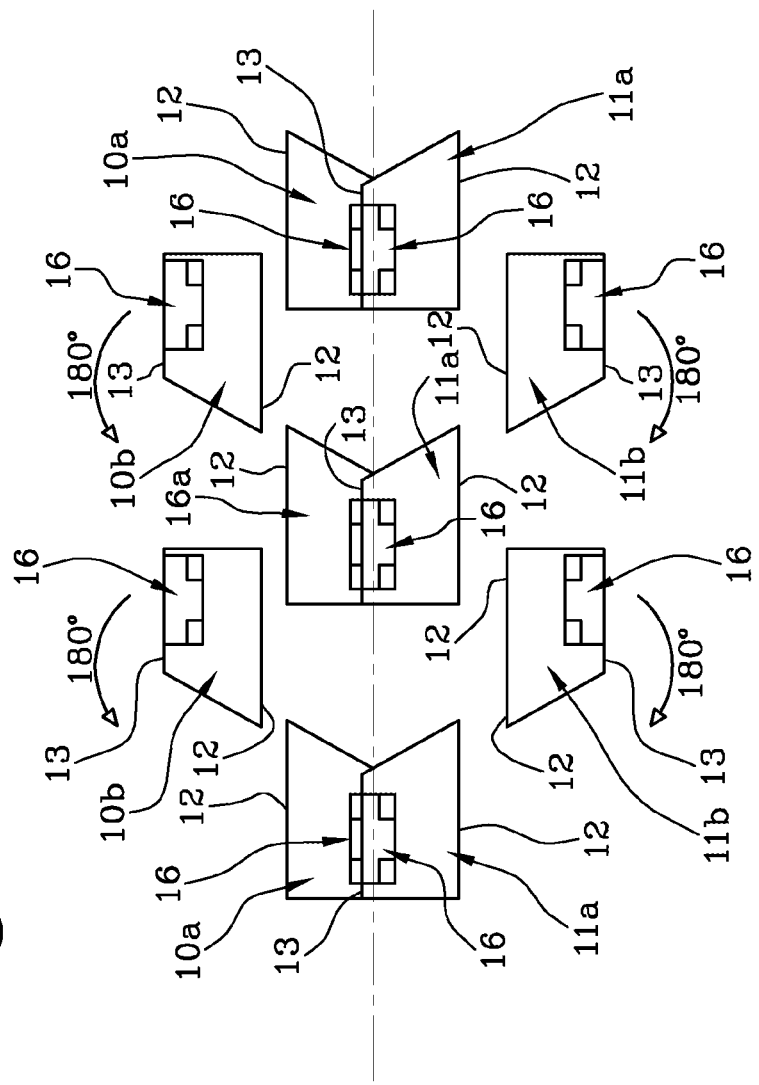
FIG. 12 shows a schematic view of a fourth step of a second embodiment of the method according to this invention.
Figure 16:
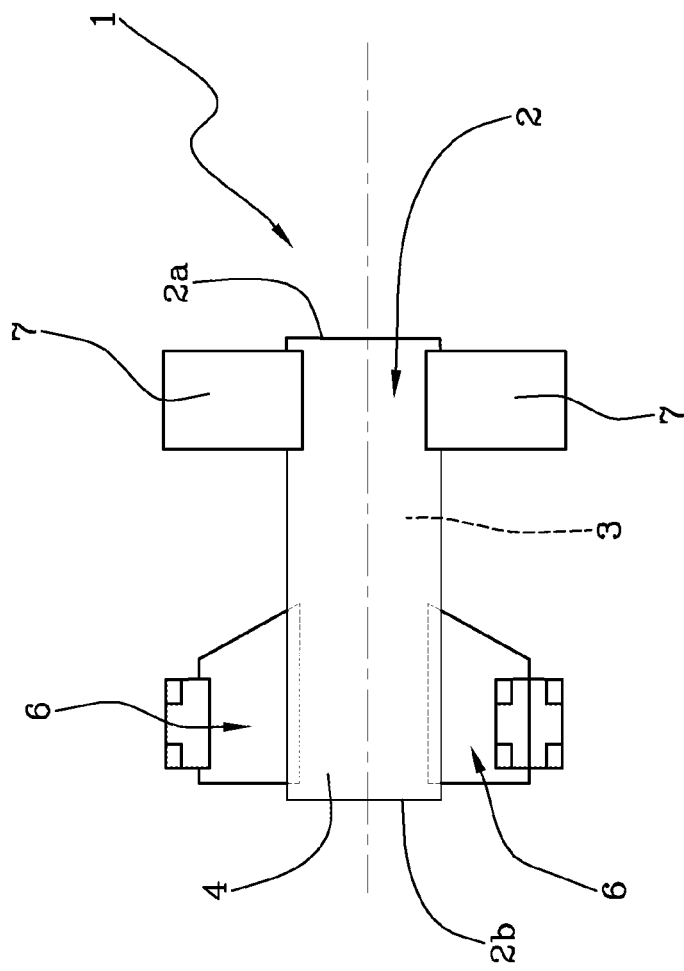
FIG. 16 shows a schematic plan view of an absorbent sanitary article made using the method of FIGS. 9 to 15.

With reference to the accompanying drawings, the numeral 1 denotes an absorbent sanitary article made with a method according to this invention and illustrated schematically in FIGS. 8 and 16.

More specifically, the term "absorbent sanitary article" is used in this text to denote a nappy for children or adults, or an undergarment provided with a central absorbent portion and a plurality of side accessory elements.

The accessory elements are preferably flaps or elastic closing elements.

The absorbent article 1 has a substantially rectangular shape extending along a longitudinal axis "A".

The absorbent sanitary articles 1 comprise a main body 2, or chassis, extending along the axis "A", from a front portion 2a to a rear portion 2b.

More specifically, the main body 2 of each absorbent article 1 is a composite item comprising at least one internal absorbent pad 3, normally made from cellulose fibres or SAP, placed inside a soft container defined, on one side, by a permeable sheet 4 of "non-woven fabric", or top sheet, and on the other side, by an impermeable sheet 5 of polyethylene, or back sheet.

In some embodiments (not illustrated) the impermeable sheet is in turn covered by a further permeable sheet.

The main body 2 is made from a first web 21, preferably defining the top sheet, on which a further web 24 (preferably forming the back sheet) and the pad 25 are subsequently superposed and connected.

Preferably, also, there are more than three layers inside the article, but the technical details will not be described as the nappy structure is of essentially known type.

Pairs of accessory elements 6, or flaps, projecting transversely to the axis "A", are fixed at the end portions (front portion 2a and/or rear portion 2b) of the main body 2. More specifically, the lateral flaps 6 extend from the rear portion 4 of the absorbent article 1 and are, in use, designed to be placed over respective fastening zones of the front portion 2a in order to close the absorbent article 1 round the wearer's waist.

In some embodiments, the rear portion 2b is also provided with respective flaps 7, which usually, but not exclusively, are different in nature and shape.

According to one aspect of this invention, the flaps 6 or 7 are made from two strips 10, 11 of material suitable for the purpose, which are then cut into a plurality of pieces forming the flaps.

Preferably, the material is at least partially elastic so as to allow easy closing of the absorbent sanitary article 1.

Hereinafter, since the invention is focussed on the method for making the article, explicit reference is made to the pieces 10a, 10b, 11a, 11b instead of the flaps 6 or 7.

More preferably, the method comprises preparing a second continuous web 22 of material suitable for making the flaps 6 extending along a respective longitudinal direction "B" and dividing the second web 22 along the longitudinal direction "B" for making the two strips 10, 11.

In other words, a first strip 10 and a second strip 11 are made from a single web (the second web 22) cut along its direction of extension.

Preferably, the pair of longitudinal strips 10, 11 are substantially parallel with each other. It should be noted that the term "parallel" is not used to mean that the two strips 10, 11 are necessarily coplanar, but they might also lie in offset planes which, for reasons of space, facilitate the making of the movement means.

The strips 10, 11 are fed along the respective main direction at a speed which is typical of machines for making absorbent sanitary articles (for example, 5-400 m/s).

Preferably, each strip is divided into a succession of pieces 10a, 10, 11a, 11b by at least one cutting unit (preferably a cutting drum).

Preferably, cutting is performed without producing any waste (zero-waste).

It should be noted that the pieces 10a, 10b, 11a, 11b are trapezoidal in shape, each having a long base 12 and a short base 13, and are adjacent to each other. The long base 12 and the short base 13 are both part of the longitudinal edges of the respective strip 10, 11.

Thus, the pieces 10a, 10b, 11a, 11b of each strip 10, 11 can be divided alternately into first pieces 10a, 11a, having a first orientation, and second pieces 10b, 11b, having a second orientation opposite to the first orientation.

The orientation is defined by the relative position of the long base 12 and of the short base 13 of each piece. Each strip 10, 11 thus comprises an alternating succession of first pieces 10a, 11b having a first orientation, and second pieces 10b, 11a having a second orientation.

In the embodiment illustrated, and for illustrative purposes only, the two strips are parallel and facing each other and:

the short base 13 of each first piece 10a of the first strip 10 is oriented towards the second strip 11;

the long base 12 of each second piece 10b of the first strip 10 is oriented towards the second strip 11;

the long base 12 of each first piece 11b of the second strip 11 is oriented towards the first strip 10;

the short base 13 of each second piece 11a of the second strip 11 is oriented towards the first strip 10.

Thus, the first strip 10 is divided into a succession of first pieces 10a and second pieces 10b which are trapezoidal in shape in such a way that the first pieces 10a have a first orientation, with the short base 13 oriented towards the second strip 11, and the second pieces 10b have a second orientation, with the long base 12 oriented towards the second strip 11.

Similarly, the second strip 11 is divided into a succession of first pieces 11b and second pieces 11a which are trapezoidal in shape in such a way that the first pieces 11b have a first orientation, with the long base 12 oriented towards the first strip 10, and the second pieces 11a have a second orientation, with the short base 13 oriented towards the first strip 10.

In the preferred embodiment, the pieces of one strip 10, 11 are oriented in mirror-like fashion relative to the corresponding pieces of the other strip, so that the first pieces 10a, 11b face the respective second pieces 10b, 11a of the other strip.

It should, however, be noted that the strips 10, 11 might not be facing and might be fed from different directions.

Nevertheless, the descriptions of the orientations in the embodiments illustrated are more than adequate for a person skilled in the art to understand how the pieces must be oriented as a function of the position and feed direction of the strips.

Preferably, the pieces 10a, 10b, 11a, 11b all have the same shape.

It should be noted that the method can be implemented with pieces having any trapezoidal shape.

In a preferred embodiment, the pieces 10a, 10b, 11a, 11b have the shape of a right-angled trapezium.

Alternatively, all the pieces might have the shape of an isosceles trapezium or a scalene trapezium (preferably acute).

According to one aspect of the invention, the method comprises a step of rotating the first or second pieces 10b, 11a of each strip 10, 11 by 180° (in the plane of the piece) in such a way as to give the pieces 10a, 10b of the first strip the first orientation and the pieces 11a, 11b of the second strip the second orientation.

In other words, the method comprises rotating the pieces having the "wrong" orientation with reference to an open condition of the absorbent sanitary article 1.

For this reason, with reference to the embodiment illustrated, rotation is performed on those pieces 10b, 11b whose long bases 12 face each other, whilst the first pieces 10a, 11b whose short bases 13 face each other maintain the same (first) orientation, at least relative to each other.

Thus, after the rotating step, all the pieces 10a, 10b of the first strip 10 have a first orientation and are aligned with each other in succession.

Similarly, all the pieces 11a, 11b of the second strip 11 have a second orientation and are aligned with each other in succession.

As stated above, defining which are the pieces to be rotated with reference to the adjacent strip is purely exemplary and explanatory.

Preferably, there is also a step for spacing the pieces 10a, 10b, 11a, 11b of each strip 10, 11 in such a way as to allow aligning the pieces 10a, 10b, 11a, 11b which (all) have the same orientation.

Preferably, the spacing step is carried out along the movement direction "A".

For this reason, each first piece 10a of the first strip 10 is spaced axially from two second pieces 10b adjacent to it.

Similarly, each first piece 11a of the second strip 11 is spaced axially from two second pieces 11b adjacent to it.

It should be noted that the spacing step can be performed either before, after or at the same time as rotation.

In the preferred embodiment, the two steps are performed substantially simultaneously.

In a first embodiment the first pieces 10a, 11a and the second pieces 10b, 11b, after cutting, travel along different trajectories, for example, each on a predetermined drum, in such a way that each second piece 10b, 11b can be rotated without the first adjacent pieces obstructing its movement.

Moreover, in this way, the first pieces 10a, 11a and the second pieces 10b, 11b may be then spaced apart and synchronized independently.

It should be noted that, at least at the end of the spacing step and of the rotation step, each first piece 10a, 11b of a strip 10, 11 defines, in conjunction with a corresponding second piece 10b, 11a of the other strip, a pair of front or rear pieces to be applied on the first web 21.

Thus, each first piece 10a of the first strip 10, together with the corresponding second piece 11a of the second strip 11, defines a pair of pieces.

Similarly, each second piece 10b of the first strip 10, together with the corresponding first piece 11b of the second strip 11, defines a pair of pieces.

Preferably, to make the method more reliable, in particular in the production of absorbent articles for adults, the short bases 13 of the pieces 10a, 10b, 11a, 11b of each pair, after being rotated, are superposed and connected.

Following rotation, each piece 10a, 10b, 11a, 11b is applied on a first face 21a, in use, outer face, of the first web 21, in such a way that the long base 12 of the piece 10a, 10b, 11a, 11b protrudes laterally from the edge of the first web 21.

Preferably, the piece 10a, 10b, 11a, 11b is also fixed, by means of ultrasonic sealing or other suitable and removable means, to the first face 21a of the first web 21.

Next, or at the same time, the long base 13 of each piece 10a, 10b, 11a, 11b is folded below the first web 21 and fixed to a second face 21b, in use, inner face, of the first web 21.

It should be noted that the fixing of the long base 13 to the second face 21b of the first web 21 is performed preferably using adhesive or ultrasonic sealing, or any other means designed to withstand a pulling action by a user.

Preferably, the first web 21 defines the top sheet 3 of the main body 2 of the nappy 1.

Alternatively, however, the first web 21 might define the back sheet of the main body.

Advantageously, in any case, thanks to this method the pieces do not define any obstruction to the side of the first web 21, thus facilitating its movement.

Preferably, the method also comprises a step of preparing a plurality of connecting elements 16 for the pieces 10a, 10b, 11a, 11b and a subsequent step of applying the connecting elements 16 on each of the strips 10, 11 or on the pieces 10a, 10b, 11a, 11b.

The connecting elements 16 referred to in this text mean those protrusions which are attached to the pieces (or side flaps 6) and which allow them to be fixed when the absorbent sanitary article 1 is closed.

The connecting elements 16 may be defined solely by a connecting layer or tape 17, for example adhesive, placed on the piece, or by the combination of a flap of material (or hook) 17 on which the connecting layer 18 is applied.

Preferably, the connecting elements 16 are applied on each strip 10, 11 in such a way that they are offset and positioned on both of the longitudinal edges of the strip 10, 11.

More specifically, the spacing (or distance measured along the direction of extension of the strip 10, 11) between two connecting elements 16 of a single edge is equal to the sum of the short base 13 and the long base 12 of the pieces 10a, 10b, 11a, 11b.

Moreover, the distance or spacing between two connecting elements 16 of two opposite edges in a single strip 10, 11 is variable between a value less than the short base 13 and a value greater than the long base 12, depending on the embodiment of the nappy.

It should be noted that the connecting elements 16 are applied on each strip 10, 11 (or on the pieces), in such a way that at least one flap 16a projects laterally from the respective strip 10, 11 (or from the pieces). In light of this, the method comprises a step of folding the projecting flap 16a below the respective strip 10, 11 (or piece).

In the preferred embodiment, the connecting elements 16 are also made in line.

In other words, the preparing step comprises providing a third continuous web 23 of material suitable for making the plurality of connecting elements 16 and then subdividing the third web 23 into a plurality of separate portions 19 defining the individual connecting elements 16.

There is also a step of applying the joining layer 17 on each connecting element 16 (that is to say, on each separate portion 19).

The invention achieves the preset aims and brings important advantages.

In effect, implementing a method whereby the pieces are positioned on the web or on the chassis in such a way that they remain within the overall dimensions makes the design of machines very easy, in terms of dimensions, for making absorbent sanitary articles for adults.

Moreover, the application of the pieces on the top sheet of the main body, with subsequent folding below, makes it possible to avoid the need for connecting the pieces to the main body by more invasive and less efficient gluing or fixing systems.

The invention claimed is:

1. A method for making absorbent sanitary articles, comprising the steps of:
feeding along a longitudinal direction of movement a continuous first web defining at least part of a top sheet or a back sheet of a main body of an absorbent sanitary article, the first web including an outer first face and an inner second face that is couplable with a continuous further web for delimiting the main body of the absorbent sanitary article;
feeding a pair of longitudinal strips;
dividing each of the pair of longitudinal strips into a succession of trapezoidal pieces adjacent to each other, with each of the trapezoidal pieces including a long base and a short base, such that the trapezoidal pieces of each of the pair of longitudinal strips are divided alternately into first pieces having a first orientation and second pieces having a second orientation opposite to the first orientation;
spacing the trapezoidal pieces of each of the pair of longitudinal strips from each other;
rotating the first pieces or second pieces of each of the pair of longitudinal strips by 180° in a plane to give the pieces of the first strip the first orientation and the pieces of the second strip the second orientation;
applying each of the trapezoidal pieces on the outer first face such that the long base of the each of the trapezoidal pieces protrudes laterally from an edge of the first web;
folding the long base of the each of the trapezoidal pieces towards the inner second face and fixing the long base of the each trapezoidal pieces to the inner second face.

2. The method according to claim 1, wherein after the rotating and spacing steps, associating each first piece of one of the pair of longitudinal strips with a corresponding second piece of the other of the pair of longitudinal strips to define a pair of front pieces or rear pieces to be applied to the first web.

3. The method according to claim 2, and further comprising a step of superposing and connecting the short bases of the trapezoidal pieces of each of the pair of longitudinal strips before or during the step of applying the each of the trapezoidal pieces on the outer first face.

4. The method according to claim 1, wherein the first web defines a top sheet of the main body of the absorbent sanitary article.

5. The method according to claim 1, wherein the trapezoidal pieces are shaped as scalene or right-angled trapeziums.

6. The method according to claim 1, and further comprising the following steps:
preparing a continuous second web of material suitable for making the trapezoidal pieces and extending along a respective longitudinal direction;
dividing the second web along the longitudinal axis for making the pair of longitudinal strips.

7. The method according to claim 1, and further comprising the following steps:
preparing a plurality of connecting elements for the trapezoidal pieces;
applying the connecting elements on each of the pair of longitudinal strips or on the trapezoidal pieces.

8. The method according to claim 7, wherein the step of preparing the plurality of connecting elements comprises the following sub-steps:
preparing a continuous third web of material suitable for making the plurality of connecting elements;
dividing the third web into a plurality of separate portions defining the individual connecting elements.

9. The method according to claim 7, and further comprising a step of applying a joining layer on each connecting element.

10. The method according to claim 7, and further comprising:
  applying the connecting elements on each of the pair of longitudinal strips or on each of the trapezoidal pieces such that a projecting flap projects laterally from the respective each of the pair of longitudinal strips or each of the trapezoidal pieces;
  folding the projecting flap below the respective each of the pair of longitudinal strips or each of the trapezoidal pieces.

11. The method according to claim 7, and further comprising applying the connecting elements on each of the pair of longitudinal strips in such that the connecting elements are offset and positioned on both longitudinal edges of the each of the pair of longitudinal strips, and a spacing between two connecting elements of a same edge is equal to a sum of the short base and the long base of each trapezoidal piece.

12. The method according to claim 1, wherein the spacing step is carried out along the movement direction and according to a predetermined spacing.

13. The method according to claim 1, wherein the pair of longitudinal strips are parallel to each other.

14. The method according to claim 1, wherein the dividing is performed without producing any waste.

15. A method for making absorbent sanitary articles, comprising the steps of:
  feeding along a longitudinal direction of movement a continuous first web defining at least part of a main body of an absorbent sanitary article, the first web including an outer first face and an inner second face;
  feeding a pair of longitudinal strips;
  dividing each of the pair of longitudinal strips into a succession of trapezoidal pieces adjacent to each other, with each of the trapezoidal pieces including a long base and a short base, such that the trapezoidal pieces of each of the pair of longitudinal strips are divided alternately into first pieces having a first orientation and second pieces having a second orientation opposite to the first orientation;
  spacing the trapezoidal pieces of each of the pair of longitudinal strips from each other;
  rotating the first pieces or second pieces of each of the pair of longitudinal strips by 180° in a plane to give all of the first pieces and the second pieces of the pair of longitudinal strips a same one of the first orientation or the second orientation;
  applying each of the trapezoidal pieces on the outer first face such that the long base of the each of the trapezoidal pieces protrudes laterally from an edge of the first web;
  folding the long base of the each of the trapezoidal pieces towards the inner second face of the first web and fixing the long base of the each of the trapezoidal pieces to the inner second face;
  subsequently superposing and connecting a further web to the inner second face of the first web already provided with the trapezoidal pieces, so that the long base of the each of the trapezoidal pieces remains interposed between the first web and the further web.

16. The method according to claim 15, and further comprising a step of coupling the inner second face of the first web with an absorbent pad before or at a same time as the step of superposing and connecting the further web.

* * * * *